United States Patent
Genova et al.

[11] Patent Number: 6,116,234
[45] Date of Patent: Sep. 12, 2000

[54] METERED DOSE INHALER AGITATOR

[75] Inventors: Perry A. Genova, Chapel Hill; Warren R Jewett, Cary, both of N.C.

[73] Assignee: IEP Pharmaceutical Devices Inc., Raleigh, N.C.

[21] Appl. No.: 09/241,010

[22] Filed: Feb. 1, 1999

[51] Int. Cl.⁷ .................................................. A61M 11/00
[52] U.S. Cl. .................. 128/200.23; 128/200.14
[58] Field of Search .................. 128/200.16, 200.14, 128/200.23, 203.12; 222/402.1; 366/108, 110–116, 241, 605; 239/102.2

[56] References Cited

U.S. PATENT DOCUMENTS

| | | |
|---|---|---|
| 3,183,907 | 5/1965 | Bush et al. . |
| 3,361,306 | 1/1968 | Grim . |
| 3,565,070 | 2/1971 | Hanson et al. . |
| 3,749,290 | 7/1973 | Micallef . |
| 3,970,250 | 7/1976 | Drews ................................ 128/200.16 |
| 4,206,758 | 6/1980 | Hallworth et al. . |
| 4,803,978 | 2/1989 | Johnson, IV et al. . |
| 4,842,415 | 6/1989 | Cane et al. .............................. 366/110 |
| 4,934,358 | 6/1990 | Nilsson et al. . |
| 4,955,371 | 9/1990 | Zamba et al. . |
| 5,060,643 | 10/1991 | Rich et al. . |
| 5,062,423 | 11/1991 | Matson et al. . |
| 5,190,029 | 3/1993 | Byron et al. . |
| 5,261,601 | 11/1993 | Ross et al. ........................... 239/102.2 |
| 5,284,132 | 2/1994 | Geier . |
| 5,351,683 | 10/1994 | Chiesi et al. . |
| 5,363,842 | 11/1994 | Mishelevich et al. ............. 128/200.23 |
| 5,544,647 | 8/1996 | Jewett et al. . |
| 5,622,163 | 4/1997 | Jewett et al. . |

*Primary Examiner*—Glenn K. Dawson
*Attorney, Agent, or Firm*—Pitney, Hardin, Kipp & Szuch, LLP

[57] ABSTRACT

A metered dose inhaler including a mechanism for agitating the medicament formulation prior to its separation in a measured dose, for administration to a mammal, including a human. The separated dose is a homogeneous mixture of prescribed medicine in a fluid carrier.

7 Claims, 3 Drawing Sheets

METERED DOSE INHALER AGITATOR

BACKGROUND OF THE INVENTION

1. Field of the Invention

The invention relates to dispensers of fluid dispersions.

2. Brief Description of Related Art

A wide variety of fluid dispensers are known and commercially available to dispense metered proportions of a contained fluid from containers. For example, U.S. Pat. No. 3,749,290 describes a trigger actuated dispensing pump assembled with a fluid container. Upon actuation, a measured proportion of the contained fluid is dispensed from the containers.

Of particular importance as fluid dispensers are metered dose inhalers (MDI) employed to administer fluid medications to animals, including humans.

The use of inhalers is well known and the art has developed over the past twenty five years to cover many versions of the basic concept of a "pumping" type medication applicator. The device may be manually pumped (such as described in U.S. Pat. No. 5,284,132) or a pumping like cycle may be utilized. The medication may also be repeatedly released from a pressurized disposable canister to create repeated sprays or inhalations as needed.

Representative of the early inhalers for oral and intranasal administration of medications are those described in, for example, U.S. Pat. Nos. 3,361,306; 3,183,907; 3,565,070; 4,206,758; 4,803,978; 4,934,358; 4,955,371; 5,060,643; and 5,351,683. Representative of nasal-pharyngeal inhalers for large mammals such as a horse is that described in U.S. Pat. No. 5,062,423.

Metered dose inhalers (MDIs) are, at present, the most efficient and best-accepted means for accurately delivering medications in small doses to an animal's respiratory tract. Therapeutic agents commonly delivered by the inhalation route include bronchodilators ($B_2$ agonists and anticholinergics) corticosteroids, and anti-allergics. Inhalation may also be a viable route for anti-infective, vaccinating, systemically acting and diagnostic agents, as well as anti-leukotrienes, anti-proteases and the like.

MDIs are available in several types. Most frequently, MDIs comprise a pressure resistant container (canister) typically filled under super-atmospheric pressures with a product such as a drug dissolved in a liquefied propellant, or micronized particles suspended in a liquefied propellant. The container is fitted with a metering valve. The valve is movable from an inner (charging) position to an outer (discharging) position. A spring bias holds the valve in the charged position until forced to the discharge position. Actuation of the metering valve allows a metered portion of the canister content to be released, whereby the pressure of the liquefied propellant carries the dissolved or micronized drug particles out of the container and to the patient. A valve actuator also functions to direct the aerosol as a spray into the patient's oropharynx.

Surfactants are usually dissolved in the aerosol formulation and can serve the dual functions of lubricating the valve and reducing aggregation of micronized particles.

Representative of pharmaceutical formulations for use in metered dose inhalers are those described in U.S. Pat. No. 5,190,029. The MDI devices for administering such pharmaceutical formulations are also well known as seen for example in the descriptions given in U.S. Pat. Nos. 3,361,306; 3,565,070; and 4,955,371 which are incorporated herein by reference thereto.

A disadvantage arising from use of the known devices is that the patient cannot control the uniform dispersion of medicament in the aerosol container at any given time. The containers are generally not transparent to view, being light protective of the contents. Shaking them is not always practical to assure homogeneous, uniform dispersion of solid particles in the liquid carrier. Generally, homogeneous dispersions of medications tend to separate in about 20 seconds due to the effect of gravity.

The modification of a conventional metered dose inhaler by the method of the present invention obviates this disadvantage in that the aerosol formulation, particularly where the medication is a solid to be dispersed in a liquid carrier, is mixed to homogeneity immediately prior to charging of the metering valve for subsequent release.

SUMMARY OF THE INVENTION

An assembly for administration to the respiratory tract of a mammal orally or intranasally, a pharmaceutically active medication, which comprises;

(a) a hollow tube having
  (i) a first open end adapted by size and configuration to receive an aerosol canister containing a plurality of unit doses of the medication, in the tube hollow;
  (ii) a second open end adapted by size and configuration to couple with the oral or nasal cavities of a mammal;

(b) an aerosol canister having a top and a bottom and a metering valve on the canister top for the release of a predetermined dose of a contained medication for administration to a mammal, positioned in the first open end of the tube;

(c) means for the valved release of a unit dose of medication from the aerosol canister; and (d) means for agitating the medication in the aerosol canister, whereby a homogeneous mixture of the aerosol is obtained for release.

BRIEF DESCRIPTION OF THE DRAWINGS

Embodiments of the present invention will be described with reference to the accompanying drawings in which.

DETAILED DESCRIPTION OF THE PREFERRED EMBODIMENTS OF THE INVENTION

Figure 1:
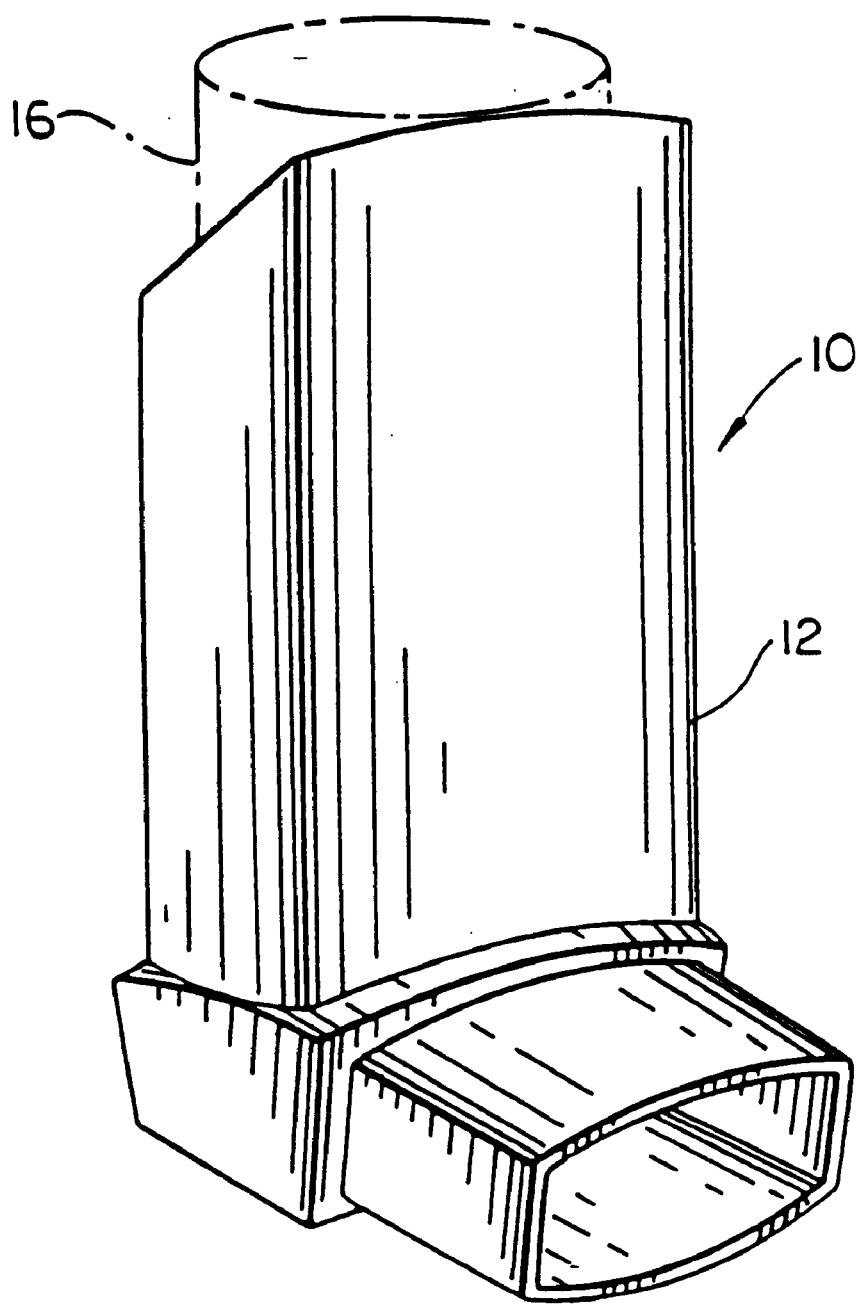
FIG. 1 is a perspective view of an embodiment metered dose inhaler of the invention shown in assembly with a metered dose inhaler aerosol canister.
Figure 2:
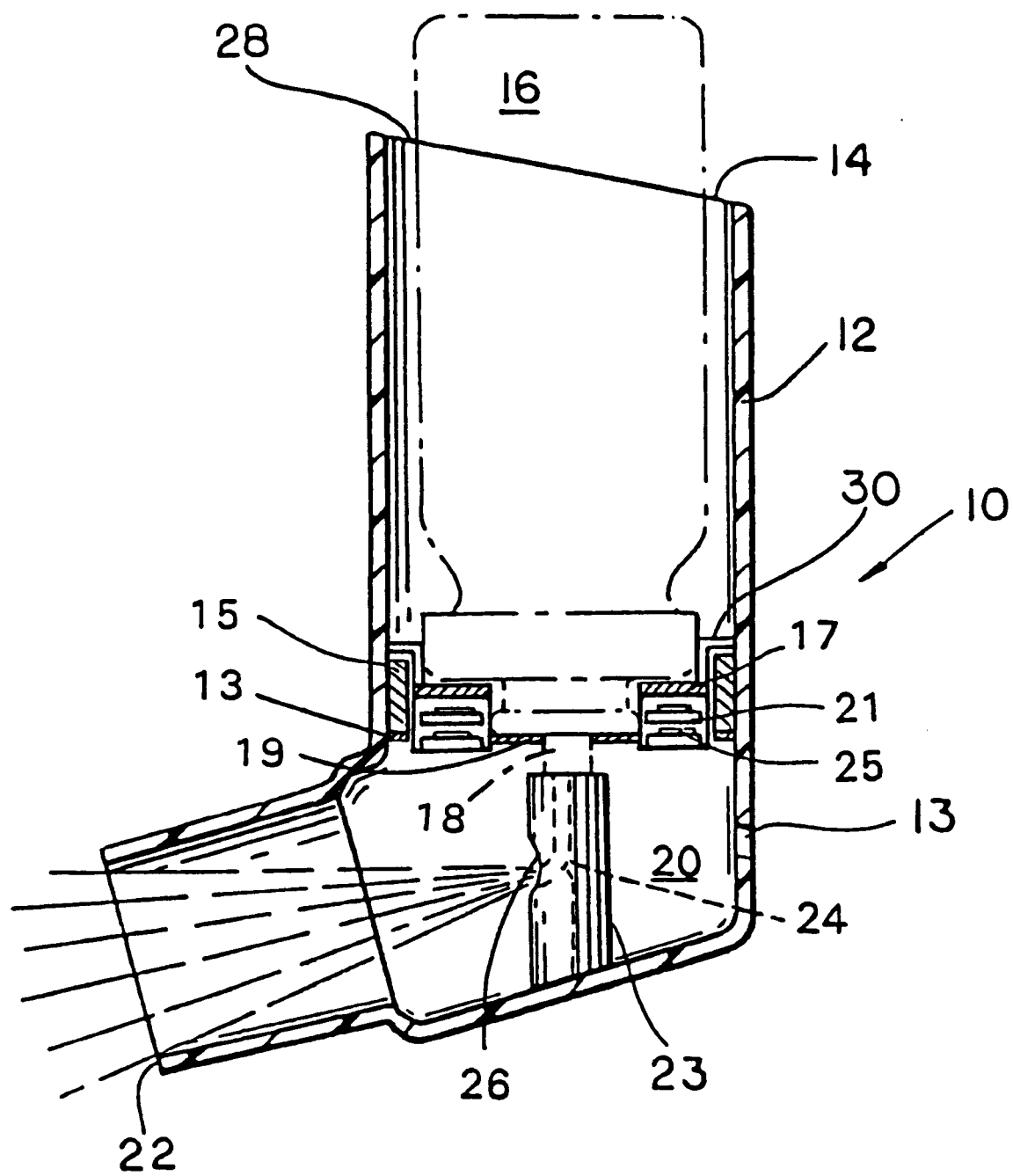
FIG. 2 is a cross-sectional side view of the assembly shown in FIG. 1.
Figure 3:
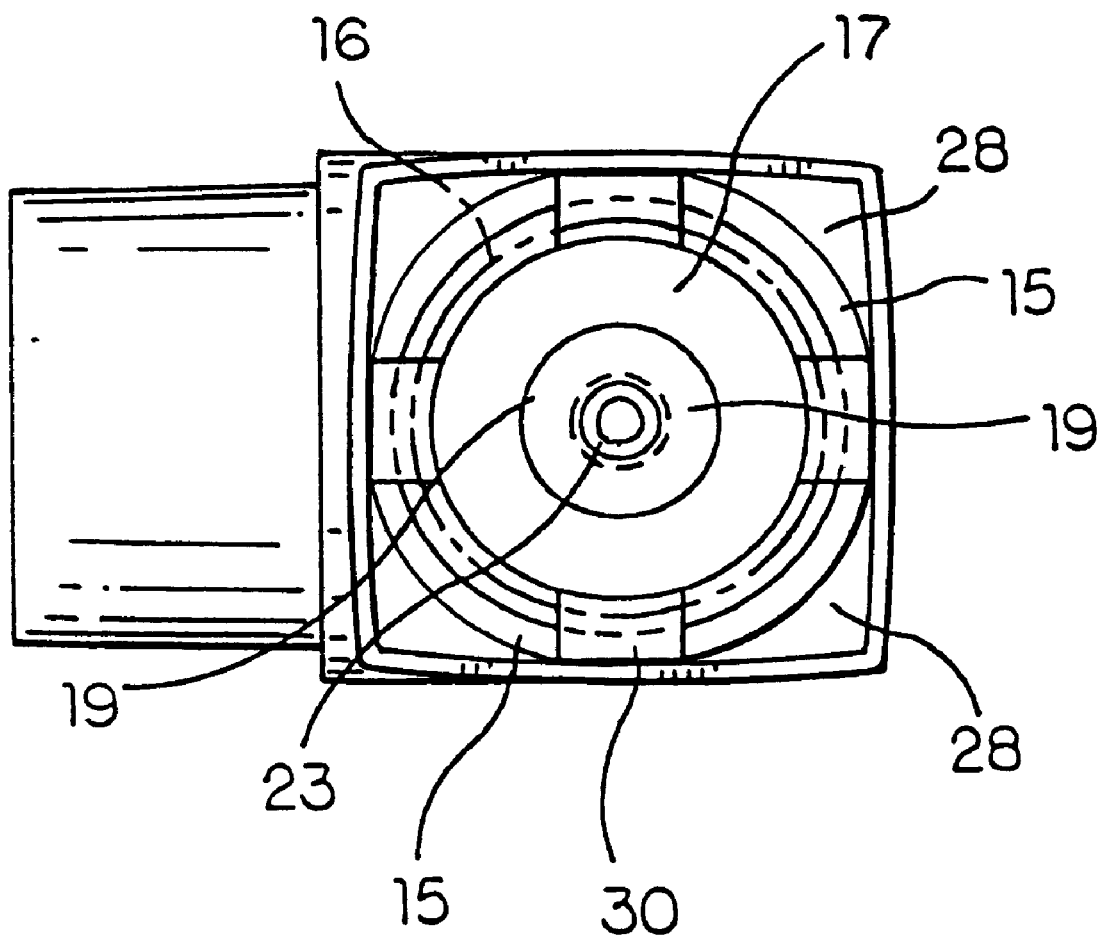
FIG. 3 is a top plan view of the assembly shown in FIG. 1.

Those skilled in the art will gain an understanding of the invention from a reading of the following description of the preferred embodiments when read in conjunction with a viewing of the accompanying drawings of FIGS. 1–3, inclusive.

FIG. 1 is a view-in-perspective of an embodiment assembly 10 of the invention, which comprises an open ended, hollow tube 12 assembled with an aerosol canister 16. The assembly 10 is a metered dose inhaler, as is known and conventional in the prior art, but improved by the inclusion of means for agitating the contents of aerosol canister 16 immediately prior to dispensation of a dose, in order that a homogeneous dispersion of medicament is dispensed. This means for agitation will be described more fully hereinafter and functions from structure internal to tube 12 and mounted within the hollow 20 of tube 12.

FIG. 2 is a cross-sectional side elevation of the assembly 10 shown in FIG. 1, and depicts further structural details of the embodiment assembly of the invention. As shown in FIG. 2, there is seen a cross-sectional side elevation of an embodiment metered dose inhaler 10 of the invention. The inhaler 10 is essentially a hollow tube 12 having a first open end 14, which by size and configuration is adapted to receive in assembly an aerosol canister 16. A small vent aperture 13 may be advantageous to vent the tube 12 during use, allowing ambient air in. The aerosol canister 16 is fitted with a conventional metering valve (not seen in FIG. 2) and spray stem 18. Such 10 canisters 16 are commercially available from the Bespak Co., North Carolina, U.S.A. They may contain any of the pharmaceutical preparations conventionally used in oral and nasal medicators, such as described for example in the U.S. Pat. No. 5,190,029. The assembled tube 12 and canister 16 locates the canister 16 partially within tube 12 hollow 20. Open end 22 communicates with hollow 20 and is adapted by size and configuration to form a mouthpiece for insertion in the oral cavity of a patient and to couple or sealingly engage with the oral lips for inspiration and expiration of the breath of a mammal. Alternatively, end 22 can be adapted to engage with the patient's nasal passages. Within the hollow 20 is fixedly mounted a spray directing element 23 which includes a continuous internal conduit 24. The conduit 24 couples with the stem 18 of the aerosol canister 16 and directs a metered dose therefrom out of nozzle 26 as a spray toward the open end 22 of the tube 12 when the canister 16 is pushed downwardly by the user. The valve of canister 16 is spring loaded and activated to release a metered dose when axial movement of from about 2.0 to 3.5 mm occurs. The valve is activated when the patient pushes the canister 16 downward, forcing the stem 18 against the element 23, opening the valve mentioned above. In a preferred embodiment of the invention, an air space 28 is defined between the interior walls of tube 12 at end 14 and the walls of canister 16 (a sliding engagement) so the canister 16 will move freely within hollow 20 until stem 18 is stopped by element 23, so that air space 28 defines a flow path through which air is drawn while inhaling the dose of medicament. As shown in both FIG. 1 and FIG. 2, the upturned canister 16 slidingly engaged in the hollow 20 through end 14 is accessible to be pushed down axially on element 23. When depressed upon element 23, the valve on the canister 16 opens to release a metered dose of the aerosol formulation, through stem 18 and conduit 24 to spray from nozzle 26 towards the open end 22 of the tube 12. One dose is released from aerosol canister 16 each time it is fully depressed upon element 23. Release of pressure on canister 16 returns it to the non-depressed position, charging the valve for a future discharge of a dose when the valve is again activated by depressing canister 16 again. As shown in FIG. 2 the valve is concealed within the neck of canister 16, and functions when the stem 18 is pushed axially and interiorly of canister 16; the valve itself is not shown in the FIGS. 1–2 being conventional and within the enclosure of the canister 16 itself.

As described to this point inhaler assembly 10 is a known device, and can be, for example, as detailed in the U.S. Pat. No. 3,361,306, U.S. Pat. No. 5,544,647 or U.S. Pat. No. 5,622,163 incorporated herein by reference thereto. The known inhaler is modified as described hereinafter to manufacture the inhaler assembly 10 of the invention.

Referring again to FIG. 2, the modification comprising the improvement of the present invention can be seen. Integrally molded on the inner wall of tube 12 and circumscribing the hollow 20 is a ledge or ring stop 13 through which another vent provides for equalization of pressure during patient inspiration. Mounted on the circular stop 13 is a synthetic polymeric foam spring 15 (preferably a polyurethane or polyethylene foam) which functions to meet the shoulder of canister 16. The downward movement of the canister 16 is limited by the valve stem to a point where the valve is depressed and opened for aerosol release. Throughout the travel of the canister 16, movement downward and returning, canister 16 is held in constant contact with crystal 17 by the foam spring 15. Mounted on the assembly of stop 13 and foam spring 15, projecting into hollow 20 and the path of an axially depressed canister 16 is a ring of piezoelectric crystals 17 (such as Rochelle salts or quartz). When fully depressed in tube 12, the shoulder of canister 16 comes in surface contact with the piezoelectric crystal 17 material. Mounted on stop 13 and in a position beneath piezoelectric crystal 17 are compression switch 19, electrical circuit board 21 and A.C. power source (battery) 25. The battery 25 can be as described above. When fully depressed in hollow 20, the canister 16 is stopped as described above, pressing the piezoelectric crystal 17 against the shoulder of canister 16. The switch 19 is closed by downward motion of the valve cap of the canister 16 to energize the circuit board 21 which is connected to the power source 25. Circuit board 21 is electrically connected to each face (opposite faces) of piezoelectric crystal 17 so that when energized, electric current is transmitted to the piezoelectric crystal 17. When activated by electric current, piezoelectric crystal 17 responds with the known reverse piezoelectric effect, expanding and contracting, resulting in a resonating crystal 17. The resonating crystal 17 transmits a pressure wave, in a continuous series to the canister 16 and its aerosol contents. The pressure waves are preferably ultra-sonic (above about 20 to 30 kHz and below 40 kHz) in frequency. The activated piezoelectric crystals are in effect transducers, introducing acoustic pressure waves into the contained aerosol formulations. The pressure waves move solids (particles) longitudinally to mix them in the fluid carrier. Since activation occurs immediately before the canister 16 valve is re-charged, the aerosol charge is of a sonically mixed formulation. Generally the mixing occurs for about 50–100 milliseconds, during release or dispensing of a metered dose of medication. Solid particles in the liquid carrier are homogeneously mixed in the fluid carrier by the acoustic waves so that the charged valve holds a metered dose of well mixed and homogeneously dispersed solids, upon upward release of the canister 16. Upon release, the canister 16 moves axially upward to again close the valve in canister 16 and open switch 19, interrupting transmission of the acoustic waves. Sonic mixing of the aerosol formulation is a preferred means for agitating the medication in the aerosol canister. However, other means of mixing such as vibration, shaking, thermal, magnetic and like generators for agitation may be employed. For example, a vibrating head may be substituted for the piezoelectric crystal described above.

Referring now to FIG. 3, there is seen a top plan view of the assembly 10 shown in FIGS. 1 and 2 showing the canister 16. As can be seen, a four-legged platform 30 is provided with the space between the legs providing an air passage therethrough. Also shown in FIG. 3 is the air gap 28, foam spring 15, compression switch 19 and element 23.

Thus, the several aforementioned objects and advantages of the present invention are most effectively attained. Those skilled in the art will appreciate that many modifications of the preferred embodiment described above may be made without departing from the spirit and scope of the invention. Although a single preferred embodiment of the invention has been disclosed and described in detail herein, it should be understood that this invention is in no sense limited thereby, and its scope is to be determined by that of the appended claims.

What is claimed is:

1. An assembly for administration to the respiratory tract of a mammal orally or intranasally, a pharmaceutically active medication, which comprises;
   (a) a hollow tube having
      (i) a first open end adapted by size and configuration to receive an aerosol canister containing a plurality of unit doses of the medication;
      (ii) a second open end adapted by size and configuration to couple with the oral or nasal cavities of a mammal;
      (iii) a hollow defined by the tube wall between the first and second open ends;
   (b) an aerosol canister having a top and a bottom and a metering valve on the canister top for the release of a predetermined dose of a contained medication for administration to a mammal, positioned in the first open end of the tube;
   (c) means for the valved release of a unit dose of medication from the aerosol canister; and
   (d) means for agitating the medication in the aerosol canister, whereby a homogeneous mixture of the aerosol is obtained for release.

2. The assembly of claim 1 wherein the means for agitating comprises acoustic pressure waves transmitted to the aerosol contents of the canister.

3. The assembly of claim 1 wherein agitation of the aerosol contents takes place during the valved release of a dose of the pharmaceutically active medication.

4. The assembly of claim 1 which further comprises as the means for agitating, a piezoelectric crystal mounted in the hollow of the tube, a power source and electrical means connecting the power source to the crystal, said crystal functioning to transmit acoustic pressure waves.

5. The assembly of claim 1, wherein the means for agitating functions upon operation of the means for valved release of a unit dose.

6. The assembly of claim 5, wherein the means for valved release comprises a spray-directing stem mounted in the hollow of the tube in alignment with the axis of the tube hollow.

7. An assembly for administration to the respiratory tract of a mammal orally or intranasally, a pharmaceutically active medication, which comprises;
   (a) a hollow tube having
      (i) a first open end adapted by size and configuration to receive an aerosol canister containing a plurality of unit doses of the medication;
      (ii) a second open end adapted by size and configuration to couple with the oral or nasal cavities of a mammal;
      (iii) a hollow defined by the tube wall between the first and second open ends;
   (b) an aerosol canister having a top and a bottom and a metering valve on the canister top for the release of a predetermined dose of a contained medication for administration to a mammal, positioned in the first open end of the tube and movable from the first open end towards the second open end, along a line co-incident with the axis of the tube hollow;
   (c) a spray-directing stem mounted in the tube hollow on an axial line co-incident with the axis of the tube hollow at a point between the first and second open ends, to receive the canister when moved from the first open end towards the second open end, whereby there occurs a valved release of a unit dose of medication from the canister;
   (d) a piezoelectric crystal mounted in the tube hollow at a point to contact the canister when moved towards the second end; and
   (e) electric circuit means connected to the piezoelectric crystal for energizing the crystal when in contact with the canister.

* * * * *